United States Patent
Sugiyama et al.

(10) Patent No.: US 12,146,131 B2
(45) Date of Patent: Nov. 19, 2024

(54) TESTING APPARATUS AND TESTING METHOD

(71) Applicant: HITACHI HIGH-TECH CORPORATION, Tokyo (JP)

(72) Inventors: Kiyotaka Sugiyama, Tokyo (JP); Tetsushi Koide, Hiroshima (JP); Chihiro Uematsu, Tokyo (JP); Hiroko Fujita, Tokyo (JP); Akira Masuya, Tokyo (JP)

(73) Assignee: HITACHI HIGH-TECH CORPORATION, Tokyo (JP)

( * ) Notice: Subject to any disclaimer, the term of this patent is extended or adjusted under 35 U.S.C. 154(b) by 651 days.

(21) Appl. No.: 17/436,396

(22) PCT Filed: Mar. 4, 2019

(86) PCT No.: PCT/JP2019/008294
§ 371 (c)(1),
(2) Date: Sep. 3, 2021

(87) PCT Pub. No.: WO2020/178931
PCT Pub. Date: Sep. 10, 2020

(65) Prior Publication Data
US 2022/0145233 A1 May 12, 2022

(51) Int. Cl.
*C12M 1/34* (2006.01)
*C12Q 1/06* (2006.01)
(Continued)

(52) U.S. Cl.
CPC .............. *C12M 41/36* (2013.01); *C12Q 1/06* (2013.01); *G06T 7/0016* (2013.01); *G06T 7/62* (2017.01);
(Continued)

(58) Field of Classification Search
CPC .................. G06V 10/44; G06V 20/695; G06T 2207/30024; G06T 5/75;
(Continued)

(56) References Cited

U.S. PATENT DOCUMENTS

2010/0232674 A1  9/2010  Amakawa et al.
2015/0269411 A1  9/2015  Lee et al.
(Continued)

FOREIGN PATENT DOCUMENTS

JP  2009244253 A  * 10/2009  ......... G01N 15/1463
JP  2010-216920 A  9/2010
(Continued)

OTHER PUBLICATIONS

Korean Office Action issued on Oct. 28, 2022 for Korean Patent Application No. 10-2021-7019602.
(Continued)

*Primary Examiner* — Md M Rahman
(74) *Attorney, Agent, or Firm* — Volpe Koenig

(57) ABSTRACT

Provided is a technique for preventing erroneous recognition of a fine particle region from a captured image of fine particles. A fine particle testing apparatus of the present disclosure includes: an imaging part capturing a first fine particle image of a well that holds a liquid containing fine particles; an image processor executing a process of generating a second fine particle image by extracting a contour of the first fine particle image, a process of performing a logical operation between the first fine particle image and the second fine particle image, a process of calculating a feature amount of the fine particles based on a result of the logical operation, and a process of determining growth of the fine particles in the well based on the calculated feature amount; and an output part outputting a result of the determination.

15 Claims, 9 Drawing Sheets

(51) Int. Cl.
*G06T 7/00* (2017.01)
*G06T 7/62* (2017.01)
*G06V 10/44* (2022.01)
*G06V 20/69* (2022.01)

(52) U.S. Cl.
CPC ............ *G06V 10/44* (2022.01); *G06V 20/695* (2022.01); *G06T 2207/30024* (2013.01)

(58) Field of Classification Search
CPC . G06T 2207/20192; G06T 2207/30072; G06T 7/136; G06T 7/194; G06T 7/11; G06T 2207/10056; C12M 41/46; C12Q 1/02; H04N 7/18
USPC ........................................................ 356/336
See application file for complete search history.

(56) References Cited

U.S. PATENT DOCUMENTS

| | | |
|---|---|---|
| 2017/0096631 A1 | 4/2017 | Uematsu et al. |
| 2018/0010084 A1 | 1/2018 | Uematsu et al. |

FOREIGN PATENT DOCUMENTS

| | | | | |
|---|---|---|---|---|
| JP | 2014035614 A | * | 2/2014 | |
| JP | 2014-082957 A | | 5/2014 | |
| JP | 2015-177768 A | | 10/2015 | |
| JP | 2015-181374 A | | 10/2015 | |
| JP | 2016-136876 A | | 8/2016 | |
| JP | 7319407 B2 | * | 8/2023 | ............... C12Q 1/18 |
| KR | 10-2015-0108963 A | | 10/2015 | |
| WO | 2017/216312 A1 | | 12/2017 | |

OTHER PUBLICATIONS

Extended European Search Report issued on Oct. 12, 2022 for European Patent Application No. 19917894.8.

Massana, R., "Measurement of bacterial size via image analysis of epifluorescence preparations: description of an Inexpensive system and solutions to some of the common problems" Paper, Scientia Marina, Institut de Ciencies del Mar, Barcelona, Spain. (1997).

* cited by examiner

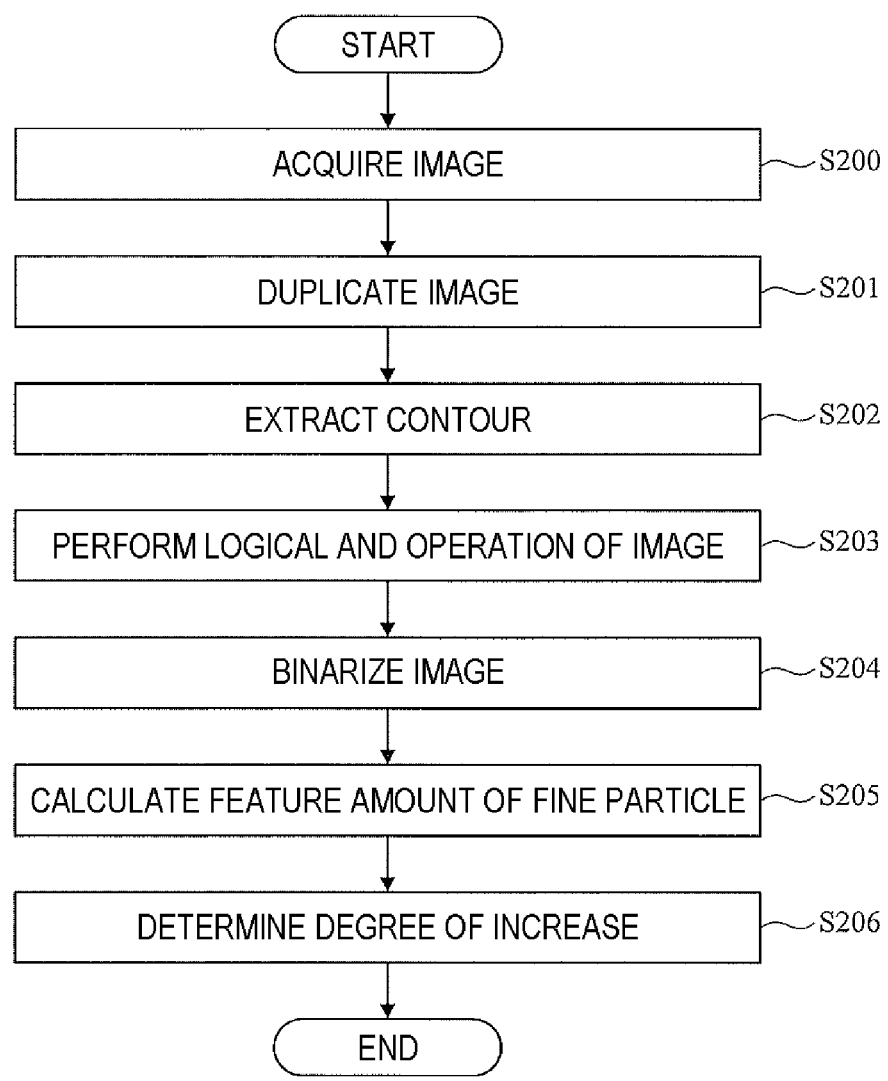

ORIGINAL IMAGE

CONTOUR EXTRACTION

LOGICAL AND

BINARIZATION

TESTING APPARATUS AND TESTING METHOD

TECHNICAL FIELD

The present disclosure relates to a testing apparatus and a testing method.

BACKGROUND ART

In analysis applications of biological samples, it is important to accurately analyze fine particles contained in a sample. Examples of fine particles present in blood, which is a typical biological sample, include blood cells such as red blood cells and white blood cells, and circulating tumor cells circulating in blood to be released from tumor tissue into blood. A test for counting the former blood cells is a general item in medical examinations and the like. Examples of techniques used for the test for counting blood cells include an electrical resistance method using a change in electrical resistance due to fine particles in a flow cell, and a flow cytometry device that optically measures scattered light and fluorescence caused by the fine particles. In addition, detection of the latter circulating tumor cells in blood is important from the viewpoint of early diagnosis of tumors, and studies for the detection of circulating tumor cells are actively progressing. As a technique for detecting circulating tumor cells in blood, for example, there is a method in which target tumor cells and other cells are separated in a minute flow path and detected by flow cytometry.

Examples of other fine particles include artificially synthesized beads. Beads are easy to modify specific functional groups on the surface thereof, and are often used to specifically bind a target biological sample molecule. For example, in a latex agglutination method, an antigen to be measured is quantified by using beads modified with antibodies. In a sample in which the antigen is present, antibodies modified on the bead surfaces are bound to each other via the antigen, and the beads are aggregated. Therefore, it is possible to measure the amount of antigen by detecting the aggregation of beads. In such a method, the amount of antigen can be measured by using an optical method, for example, a measurement method using scattered light, for aggregation of beads.

In the measurement method described above, fine particles in which the shape and number of particles do not change significantly during measurement are used as measurement targets. On the other hand, among the fine particles present in the biological sample, the shape of the particles often changes during analysis, and the number of particles often increases or decreases significantly. An example thereof is bacteria. In general, bacteria are spherical or cylindrical fine particles having a size of several μm, but if the bacteria are rich in nutrients, the bacteria grow, and the shape may change to be elongated or disappear depending on the surrounding environment. In such a case, it is difficult to accurately detect both a shape change and an increase of fine particles by a method such as an electric resistance method, scattered light, or fluorescence measurement, and thus a method using image analysis of a microscope has been proposed.

As a method using image analysis of a microscope, for example, there is a method of recognizing fine particles in an image obtained by microscopic observation. PTL 1 discloses a method of binarizing an image obtained by a phase contrast microscope to discriminate filamentous fine particles. In addition, PTL 2 discloses a method of comparing a feature amount obtained by binarization of a microscopic image with a database whose result is known in order to detect an increase in the number of fine particles.

CITATIONS LIST

Patent Literature

PTL 1: JP 2015-181374 A
PTL 2: JP 2015-177768 A

SUMMARY OF INVENTION

Technical Problem

In the fine particle discrimination method in the microscopic image disclosed in PTL 1, filamentous fine particles and other fine particles such as dust are discriminated by binarization. In addition, in the fine particle increase determination by the microscopic image disclosed in PTL 2, the feature amount of the fine particle is extracted by binarization and the determination is performed. In such a case, the threshold for binarization may be different depending on the degree of increase of fine particles, and thus the threshold for binarization is automatically determined for each image using discrimination analysis or the like.

However, in a case where the number of fine particles increases and the entire image is filled with the fine particles, or in a case where a clear image of fine particles cannot be obtained because the fine particles are present with a distribution spreading in the focal direction (depth direction) of the microscope, there is a possibility that the threshold value for binarization cannot be appropriately set.

Therefore, even if the techniques of PTLs 1 and 2 are used, in various cases where the properties of the fine particles are different for each measurement or where the fine particles overlap with each other due to a change in the degree of increase, there is a possibility that a fine particle region is erroneously recognized, for example, the fine particles cannot be correctly detected despite the presence of the fine particles.

The present disclosure has been made in view of such a situation, and provides a technique for preventing erroneous recognition of a fine particle region.

Solution to Problem

In order to solve the above problems, the present disclosure proposes a testing apparatus including: an imaging part capturing a first fine particle image of a well that holds a liquid containing fine particles; an image processor executing a process of generating a second fine particle image by extracting a contour of the first fine particle image, a process of performing a logical operation between the first fine particle image and the second fine particle image, a process of calculating a feature amount of the fine particles based on a result of the logical operation, and a process of determining growth of the fine particles in the well based on the calculated feature amount; and an output part outputting a result of the determination.

Further features related to the present disclosure will become apparent from the description of the present specification and the accompanying drawings. Problems, configurations, and effects other than those described above will be clarified by the following description of the embodiments. The description of the present disclosure is merely exemplary and is not intended to limit the claims or applications in any way.

Advantageous Effects of Invention

According to the present disclosure, it is possible to prevent erroneous recognition of a fine particle region, and thus it is possible to accurately determine the extent of increase of fine particles.

BRIEF DESCRIPTION OF DRAWINGS

FIG. 5 is a flowchart for explaining details of image processing in an image processor 106 in the first embodiment.

DESCRIPTION OF EMBODIMENTS

Figure 1:
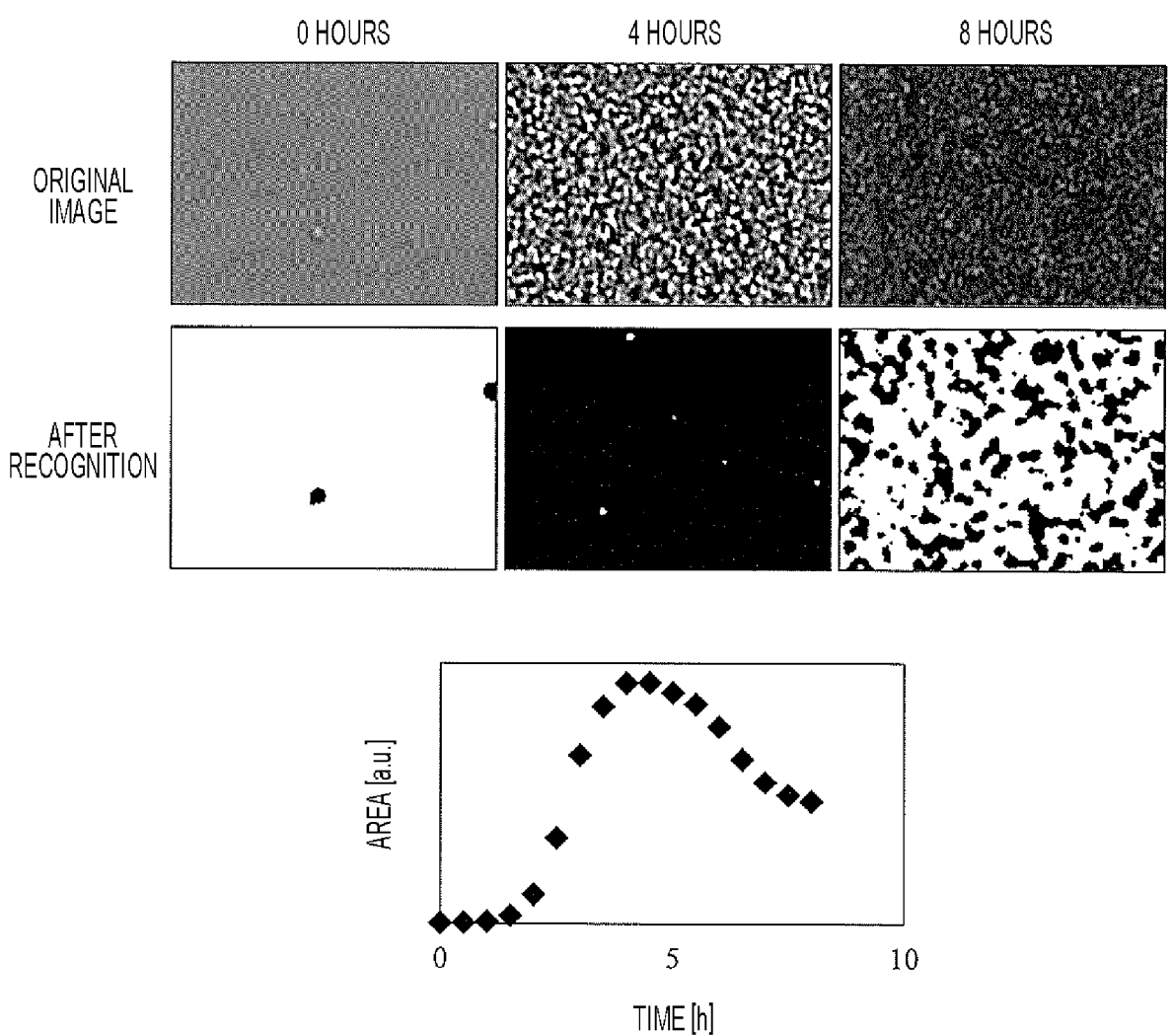
FIG. 1 is a diagram illustrating images in which a region of fine particles is erroneously recognized by binarization using discrimination analysis and an example of an increase curve.

The present embodiment discloses, for example, a technique of correctly extracting a feature amount of fine particles from an image of fine particles microscopically imaged in a well that holds a liquid containing fine particles by preventing erroneous recognition of a region where the fine particles are present, and determining a degree of increase of the fine particles. Hereinafter, embodiments of the present disclosure will be described with reference to the drawings. Note that the accompanying drawings illustrate specific embodiments based on the principles of the present technology, but these are intended to facilitate understanding of the present technology, and are not intended to be used to interpret the present disclosure in a limited manner. Note that, in the embodiments and all the drawings for describing the embodiments, components having the same function are denoted by the same reference numerals, and repeated description thereof may be omitted.

<Cause of Occurrence of Erroneous Recognition of Fine Particle Region>

FIG. 1 is a diagram illustrating images in which a region of fine particles is erroneously recognized by binarization using discrimination analysis and an example of an increase curve. With reference to FIG. 1, a cause of occurrence of erroneous recognition of a region where fine particles are present in a microscopic image will be described.

In a method of recognizing fine particles using a microscopic image and determining the degree of increase of the fine particles, an appropriate threshold for binarization may vary depending on the degree of increase of fine particles and the distribution of fine particles in a well. In a case where the number of fine particles increases and the entire image is filled with the fine particles, or in a case where a clear image of fine particles cannot be obtained because the fine particles are present with a distribution spreading in the focal direction of the microscope, there is a possibility that the threshold value for binarization cannot be appropriately set. Therefore, the number of regions recognized as fine particles by image processing may be smaller than the number of fine particles present in the image.

From the images of FIG. 1, it can be seen that the number of fine particles increases with time, and almost the entire image is filled with the fine particles in 4 hours. In addition, the increase further proceeds in 8 hours, and the fine particles are present in an overlapped manner on the entire image (the number of fine particles increases and the image becomes dark). On the other hand, the area of the fine particles after recognition (recognition by image processing) increases up to about 4 hours and then turns to decrease, and the region of the fine particles is erroneously recognized. That is, although the number of fine particles is not actually reduced and an extremely large number of fine particles are present, it is determined that the number of regions recognized as fine particles by image processing is smaller than the number of fine particles present in the image.

Figure 2:
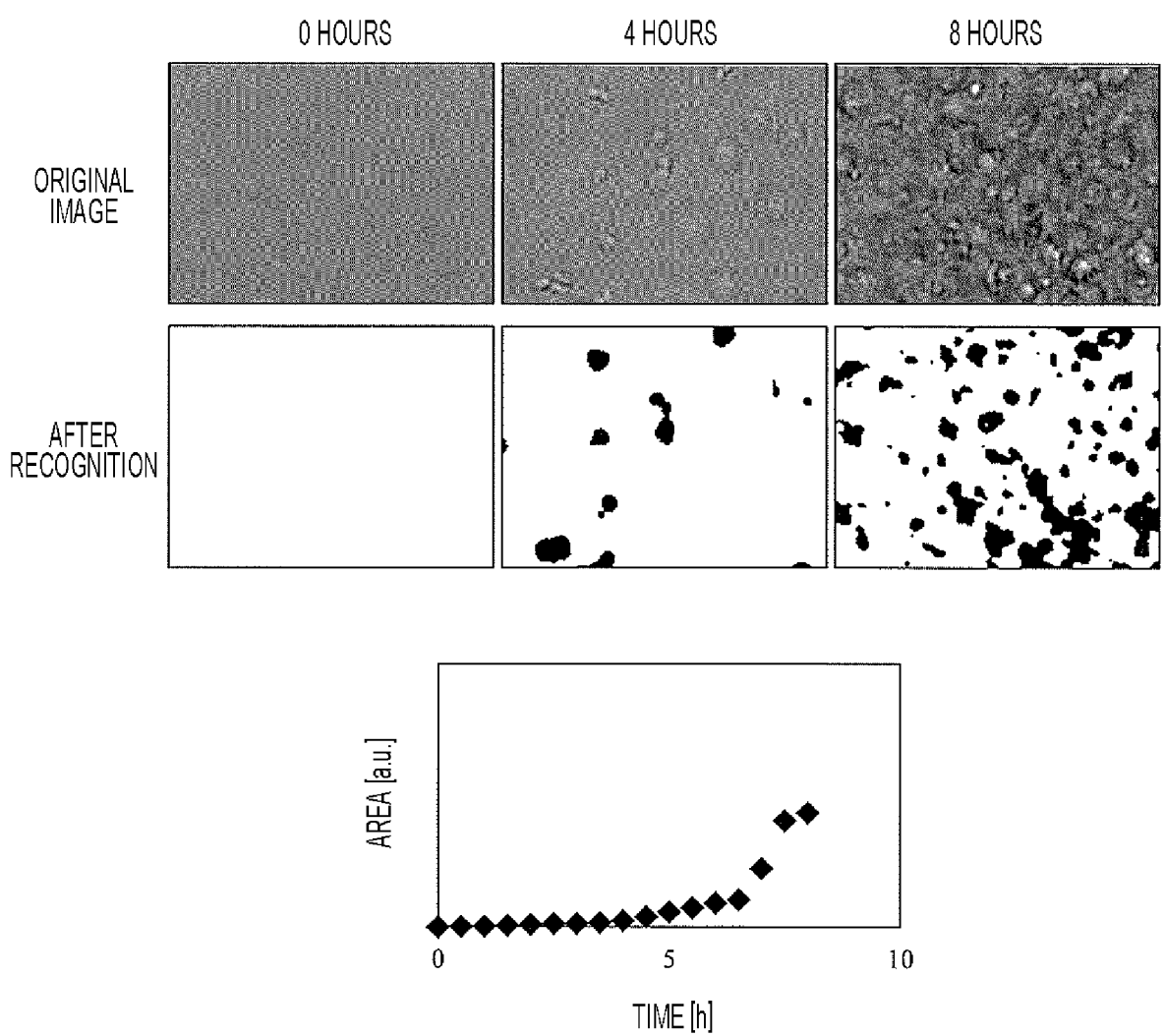
FIG. 2 is a diagram illustrating images in which a region of fine particles different from those in FIG. 1 is erroneously recognized and an example of an increase curve.

FIG. 2 is a diagram illustrating images in which a region of the other fine particles is erroneously recognized and an example of an increase curve. In the case of the result illustrated in FIG. 1, fine particles are densely present at a certain height of the well, but the other fine particles are present with a distribution spreading in the focal direction of the microscope. Therefore, in the microscopic image, there are both fine particles that are in focus and fine particles that are slightly blurred. As can be seen from the image after 4 hours in FIG. 2, the fine particles out of focus appear slightly larger than the other fine particles, and their contours are not clear. On the other hand, fine particles in focus clearly appear because of high contrast. In addition, from the image after 8 hours, although fine particles are present on almost the entire image, the fine particle region is only partially recognized as in FIG. 1.

The present embodiment proposes a technique for preventing erroneous recognition of a region of fine particles in accurately determining such a degree of increase of fine particles. Specifically, there is provided a method for determining a degree of increase of fine particles by calculating an image of first fine particles captured by a bright field microscope optical system and an image of second fine particles by contour extraction from the image of the first fine particles, performing a logical operation on the first and second images, and determining a region where the fine particles are present by binarization.

(1) First Embodiment

A first embodiment discloses an aspect in which an image of first fine particles in each well of a testing plate is acquired, an image of second fine particles is calculated by contour extraction from the image of the first fine particles, a logical operation is performed on the first and second images, and a region where the fine particles are present is determined by binarization, thereby determining a degree of increase of the fine particles.

<Configuration Example of Fine Particle Testing Apparatus>

Figure 3:
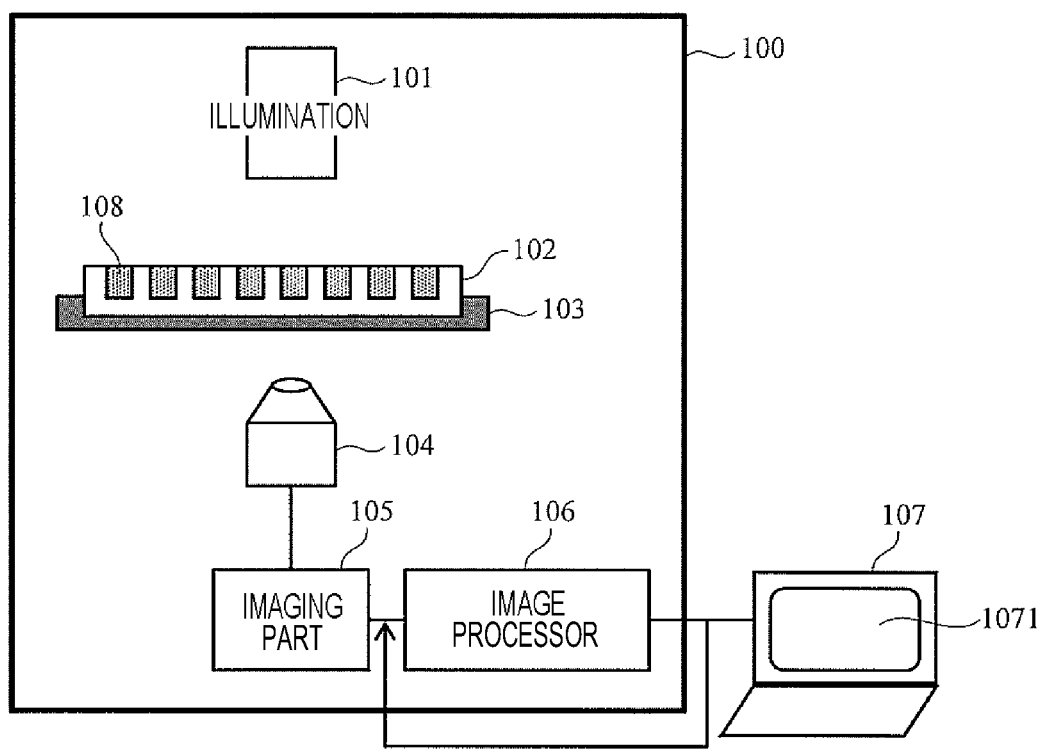
FIG. 3 is a diagram illustrating a schematic configuration example of a fine particle testing apparatus according to an embodiment of the present disclosure (common to all embodiments).

FIG. 3 is a diagram illustrating a schematic configuration example of a fine particle testing apparatus according to an embodiment of the present disclosure. A fine particle testing apparatus 100 includes an illumination part 101, a testing plate 102, a stage 103, an objective lens 104, an imaging part 105, an image processor 106, and a controller 107.

The testing plate 102 has a plurality of wells, and a sample solution 108 is held in each well. The sample solution 108 contains fine particles, and the testing plate 102 is introduced into the fine particle testing apparatus 100.

The illumination part 101 emits light toward the testing plate 102. The illumination part 101 may use white light such as a lamp or a light source such as an LED including light of a specific wavelength region. The light that has passed through each well and the sample solution 108 in the testing plate 102 is condensed by the objective lens 104, and an image is formed and captured by the imaging part 105. Then, for example, by moving the stage 103 under the control of the controller 107 and changing the relative position between the well of the testing plate and the imaging part, different wells can be imaged. The imaging operation is also controlled by the controller 107, and is executed at preset time intervals, for example, every 30 minutes. The obtained image is processed by the image processor 106 and sent to the controller 107. Here, the focal point of the objective lens 104 is preferably adjusted to the well bottom surface of the testing plate 102, but may be adjusted to the inside of the sample solution 108 away from the well bottom surface. In addition, a plurality of points in the well may be imaged, or a plurality of images of the inside of the sample solution 108 away from the well bottom surface of the testing plate 102 may be captured.

Figure 4:
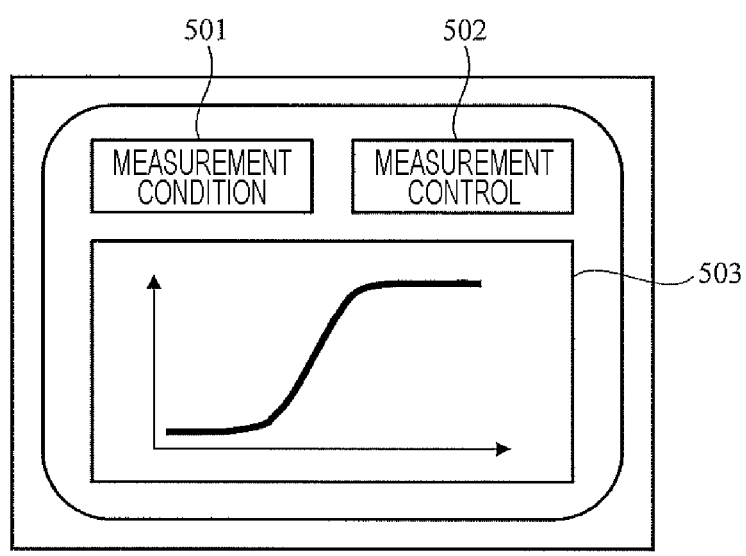
FIG. 4 is a diagram illustrating a configuration example of a graphical user interface (GUI) displayed on a display part 1071 in a first embodiment.

The controller 107 includes, for example, a general computer, a display part 1071, and the like. FIG. 4 is a diagram illustrating a configuration example of a graphical user interface (GUI) displayed on the display part 1071. The GUI can be configured to include, for example, a measurement condition input/display area 501, a measurement control state display area 502, and an increase curve display area 503. Setting of measurement conditions, start and stop of measurement, display of an increase curve, and display of a result as to whether the number of particles has increased are performed according to an instruction of an operator (user). Examples of the measurement conditions include the type of particles, the measurement time interval of images, and the discrimination time.

<Details of Image Processing>

FIG. 5 is a flowchart for explaining details of image processing in the image processor 106 in the first embodiment. Here, in the following description, the image is an 8-bit grayscale image, and a pixel value of 0 corresponds to black and a pixel value of 255 corresponds to white. The processing of the present embodiment is effective even for a grayscale image other than 8-bit images or a black-white inverted image. In addition, a color image can be converted into a grayscale image to perform similar processing.

(i) Step 200

The image processor 106 receives an image acquired by the imaging part 105 and executes processing of the following steps. Here, in an image captured under preferred conditions, the inside of fine particles often appears white and the contour thereof often appears black.

(ii) Step 201

The image processor 106 duplicates the image acquired in step 200, and stores the duplicated image in an internal memory (not illustrated) of the image processor 106 or a memory (not illustrated) of the controller 107. This duplicate image is not subjected to image processing for use in later processing and is retained in the memory as a first fine particle image.

(iii) Step 202

The image processor 106 acquires the first fine particle image from the internal memory (not illustrated) of the image processor 106 or the memory (not illustrated) of the controller 107, and performs contour extraction processing on the first fine particle image. Examples of the processing for extracting the contour of the fine particles include a variance filter. In the variance filter, a process of replacing a value of a pixel of interest with a variance value of pixels around the pixel is executed. In the pixel in which the fine particle is present, a change from the surrounding pixel in which the fine particle is not present becomes large, so that the contour of the fine particle can be extracted.

Meanwhile, in addition to the variance filter, for example, an edge extraction technique such as a Sobel filter may be used. Then, a black-white inversion process may be performed to make the processed image easily viewable. It can be interpreted that the detected fine particles become black and the background becomes white due to the black-white inversion.

The image processed in step 202 is retained, for example, as a second fine particle image in the internal memory (not illustrated) of the image processor 106 or the memory (not illustrated) of the controller 107.

(iv) Step 203

The image processor 106 reads the image of the first fine particle and the image of the second fine particle from the internal memory (not illustrated) of the image processor 106 or the memory (not illustrated) of the controller 107, and performs a logical operation on the images. In the logical operation, values of pixels at the same position in the two images are calculated (for example, a logical AND operation is performed). When the logical AND operation on the two images is performed, both the region where the contour of the fine particle can be extracted in step 202 (second fine particle image) and the dark region where the pixel value is low in the original image (first fine particle image) in step 200 can be recognized in black. That is, the contour extracted region and the dark region are extracted.

Therefore, in the image after completion of step 203, the pixel values of both (i) the fine particles having a clear contour and (ii) the fine particles having an unclear contour and appearing black by absorbing and scattering incident light due to overlapping of the fine particles with each other become low (contrast is less likely to be applied).

Note that, after step 202 or step 203, noise in the image may be removed by, for example, Gaussian filtering. The Gaussian filtering allows edges in the image to be smoothed, and in a case where there is dust or the like smaller in size than a target fine particle or in order to remove a noise component of the image, the processing of step 203 is effective.

(v) Step 204

The image processor 106 binarizes the image obtained in step 203. The pixel value of the image obtained by the logical AND operation has a width of 0 to 255 in the case of 8 bits, for example. For this reason, although it is difficult to recognize the region of the fine particles, if the region blackened by binarization of black and white is regarded as the region of the fine particles, the region of the fine particles is easily identified. In the present embodiment, since the logical AND operation is used, the image before binarization includes light-dark information corresponding to the background of the original image (first fine particle image), and binarization may be performed with a constant threshold value, but may be determined by discrimination for each image. For example, the brightness and contrast of the fine particles in the image vary depending on the light amount of the illumination part 101 and the material of the testing plate 102, and also vary depending on the density of the fine particles in the image. Therefore, for example, an optimum binarization threshold value may change over time even in the same well, and may be automatically determined for each image.

(vi) Step 205

The image processor 106 extracts a feature amount for a region recognized in black as fine particles from the binarized image obtained in step 204. Examples of the feature amount include an area, a circumferential length, roundness, lengths of a minor axis and a major axis of the fine particles, a ratio thereof, and the like. For example, instead of calculating the feature amount of each fine particle, an average value of the feature amounts of the fine particles in each image may be calculated.

Here, feature amounts may be extracted from images obtained over time, and a temporal change, a maximum value, a minimum value, or the like of each obtained feature amount may be used as a new feature amount. For example, a difference value of the feature amount between two times in the same well, a maximum value and a minimum value between certain times, and a difference value between the maximum value and the minimum value can be used as the feature amount. That is, in the subsequent step, the increase of the fine particles can be determined based on the temporal change, the maximum value, and the minimum value of each feature amount. In the increase determination, it is necessary to detect whether the fine particles (cells) are alive and increases in number. Even if the fine particles are increased, if the shape is elongated, the area is increased as an image, but the fine particles are not grown. Therefore, for example, if the maximum value and the minimum value of the roundness of the fine particles do not change over time, the bacteria appear to be increasing, but there is a high possibility that the bacteria are actually dead bacteria.

(vii) Step 206

The image processor 106 determines a degree of increase of the fine particles using the feature amount calculated in step 205. For example, a result measured in advance using a method other than image analysis may be learned as teacher data, and discrimination may be performed by creating a discriminant for determining an increase in the number of fine particles. For example, a feature amount obtained from n pieces of data is associated with information on whether or not cells are proliferated obtained by another method, to be used as teacher data. Then, when (n+1)th data (image) is input, the processing up to step 205 may be performed in the same manner as before, and the increase determination processing may be replaced by estimation and determination using the teacher data. In this case, the condition is that the data amount is accumulated to some extent for the estimation and the determination.

A series of results calculated by the image processor 106 may be displayed on the display device of the controller 107. This allows the operator to accurately recognize whether the number of fine particles has increased or not. Furthermore, for example, a result of a temporal change in the feature amount (for example, an area or the like) of the fine particles obtained in step 207 may be displayed.

<Example of Measurement Result>

Figures 6A, 6B:
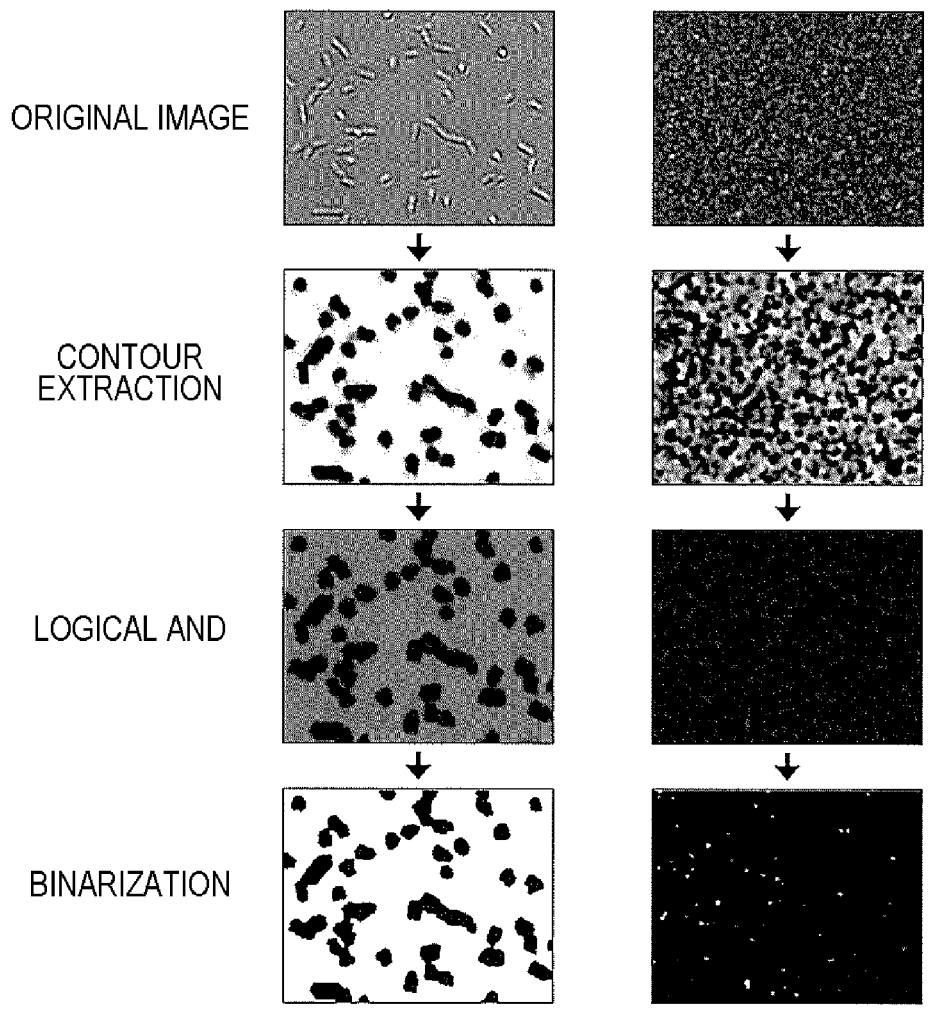
FIGS. 6A to 6B is a diagram illustrating results when the processing of steps 200 to 204 of FIG. 5 is executed on the image obtained by a fine particle testing apparatus 100.

FIGS. 6A to 6B is a diagram illustrating results when the processing of steps 200 to 204 of FIG. 5 is executed on the image obtained by the fine particle testing apparatus 100. FIG. 6A illustrates results of image processing at a lapse of two hours after the start of measurement, and FIG. 6B illustrates results of image processing at a lapse of 8 hours after the start of measurement.

FIG. 6A illustrates results of image processing in a case where the increase of fine particles has not progressed (at a lapse of two hours after the start of measurement), and each fine particle is present in an isolated manner in the image. In addition, the shape of the fine particles in the image is not uniform, and particles having a true-circular shape, an elliptical shape, and an elongated rectangular shape are mixed. In such a case, the fine particles can be extracted as black regions by the contour extraction processing in step 202. After the logical AND operation of step 203, a region that is not recognized as fine particles by the contour extraction is recognized as a gray background. Therefore, since the luminance values of the region where the fine particles are present and the background region are clearly distinguished, only the region where the fine particles are present can be correctly recognized by the binarization in step 206.

On the other hand, FIG. 6B illustrates results of image processing in a case where the number of fine particles increases and the entire surface of the image is covered with the fine particles (at a lapse of 8 hours after the start of measurement). In this case, the contour seen in FIG. 6A cannot be clearly confirmed. The increase in the number of fine particles causes the fine particles to overlap with each other, and the light from the illumination part is absorbed and scattered by the overlapping fine particles, so that most of the image appears dark, but depending on the extent of overlapping, a locally bright portion is also present. When the contour extraction processing in step 202 is executed, only such a region where the luminance value locally changes is recognized and extracted in black. In the logical operation processing of step 203, a region which satisfies either a region having a dark luminance value in the original image or a black region after contour extraction is extracted in black. Therefore, it is also possible to correctly recognize the region of the fine particles present in an overlapped manner in the original image.

That is, as illustrated in FIG. 6B, since the fine particles are overlapped over time, even if contrast appears to be applied, many fine particles are actually present, and thus the contour extraction result may not be correct. Even in such a situation, when the logical AND operation is performed, a black portion obtained by the contour extraction and a dark portion that appears black in the original image are recognized as fine particles. That is, it is recognized that the number of fine particles has entirely increased.

Effects of First Embodiment

In the first embodiment, an image of a first fine particle captured by a microscope optical system and an image of a second fine particle obtained by contour extraction from the image of the first fine particle are calculated, and a logical operation is performed on the first and second images. By doing so, it is possible to correctly recognize the fine particles not only in a case where the fine particles are present in an isolated manner, but also in a case where the number of fine particles increases and the entire image is filled with the fine particles.

(2) Second Embodiment

A second embodiment proposes effective image processing in a case where it is difficult to clearly image the contour of the fine particles in the microscope imaging as illustrated in FIG. 2, such as a case where the fine particles are present with a distribution spreading in the focal direction of the microscope. Since the fine particle testing apparatus according to the second embodiment has the same configuration as the fine particle testing apparatus 100 according to the first embodiment, the description thereof will be omitted.

<Details of Image Processing>

Figure 7:
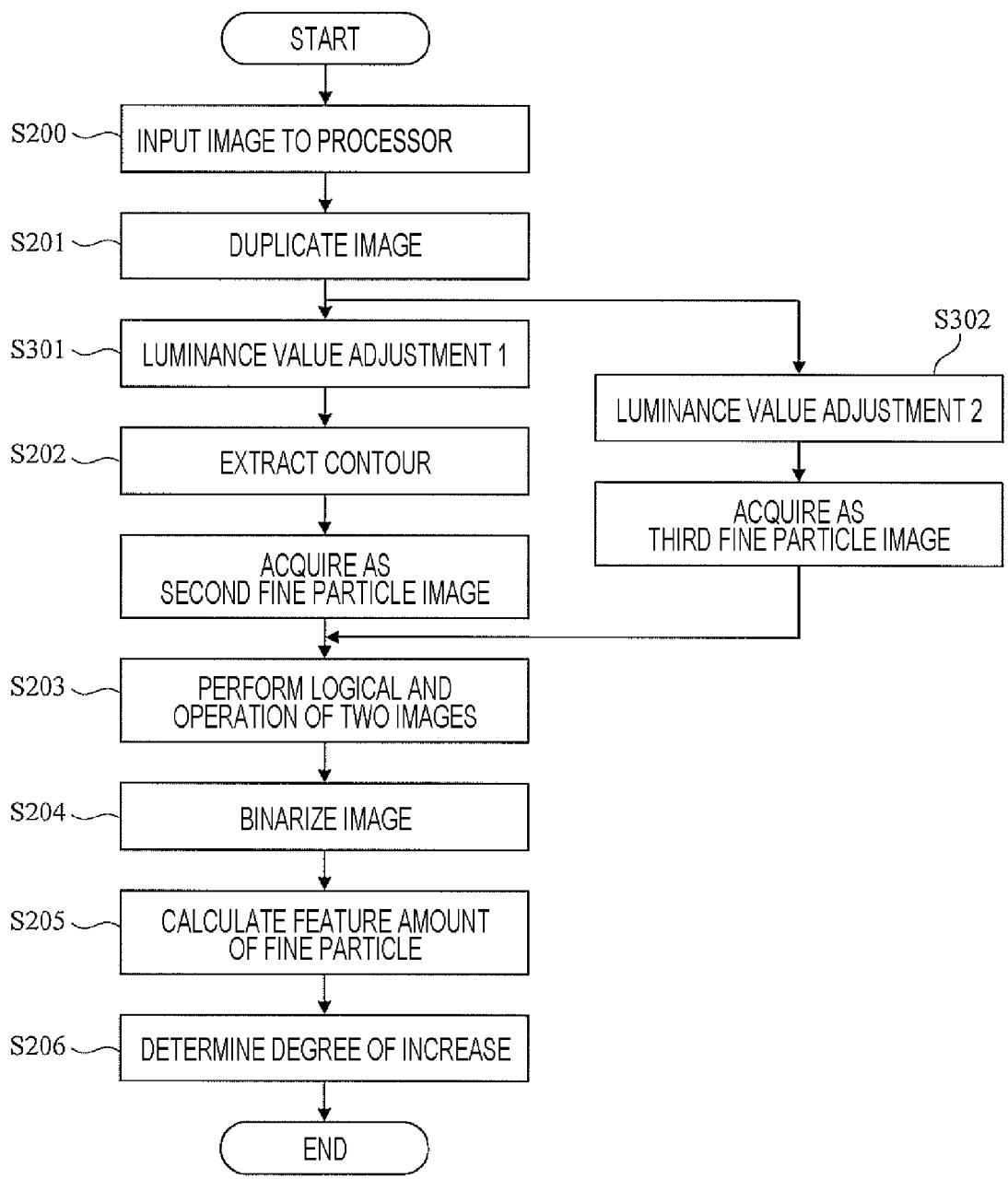
FIG. 7 is a flowchart for explaining details of image processing according to a second embodiment executed by the fine particle testing apparatus 100.

FIG. 7 is a flowchart for explaining details of image processing according to the second embodiment executed by the fine particle testing apparatus 100. In FIG. 7, processes denoted by the same reference numerals as those in FIG. 5 are as described in the first embodiment, and thus different points will be mainly described. A difference from the first embodiment is that luminance value adjustment of two types of images is added after image duplication. Here, the luminance value adjustment of the image includes contrast adjustment (luminance value adjustment 1) for changing contrast, which is a difference in brightness of the image, and light-dark adjustment (luminance value adjustment 2) for raising or lowering the luminance value of the image as a whole by a constant value.

(i) Step 301

The image processor 106 acquires the first fine particle image from the internal memory (not illustrated) of the image processor 106 or the memory (not illustrated) of the controller 107, and performs luminance value adjustment processing (luminance value adjustment 1: contrast adjustment) on the first fine particle image. Before the contour extraction, the luminance value adjustment 1 in step 301 is performed.

As described in the first embodiment, in the contour extraction, for example, a variance filter that replaces a value of a pixel of interest with a variance value of pixels around the pixel is used. In a case where the contour of the fine particle does not clearly appear, the variance value tends to be smaller than that in a case where the contour of the fine particle is clear, and the contour may not be correctly extracted. Therefore, it is effective to perform adjustment (a process of emphasizing a target pixel based on a difference in pixel value from surroundings: processed such that, for example, a portion appearing white becomes whiter and a portion appearing black becomes blacker) to increase the contrast, which is the difference in brightness of the image. By the contrast adjustment (contrast increase), even fine particles having a blurred contour can be distinguished whether the fine particles are white or black, so that the fine particles can be detected by the contour extraction in step 202. Here, the contrast adjustment processing may be executed uniformly on the entire image, may be executed only on a part of the image, or may be executed locally by dividing the image into small blocks and executing different degrees of contrast adjustment in each block.

Furthermore, for example, contrast may be applied depending on the type of cell. Bacteria having flagella move around in the sample solution, and therefore tend to blur in the focal direction (depth direction). Therefore, contrast processing may be performed. On the other hand, in the case of a cell that does not move around (a cell with low or no mobility), it is not necessary to worry about such blurring, and thus the method of the first embodiment can be used. The technique disclosed in the second embodiment is particularly effective when there is a variation in the focal direction (image blurring due to movement).

(ii) Step 202

The image processor 106 extracts the contour of the contrast-adjusted fine particle image. The extracted contour image is retained, for example, as a second fine particle image in, for example, the internal memory (not illustrated) of the image processor 106 or the memory (not illustrated) of the controller 107.

(ii) Step 302

The image processor 106 acquires the first fine particle image from the internal memory (not illustrated) of the image processor 106 or the memory (not illustrated) of the controller 107, and performs luminance value adjustment processing (luminance value adjustment 2: light-dark processing) on the first fine particle image. The light-dark processing is performed immediately before the logical AND operation on two images in step 203. The image subjected to the light-dark processing is retained as a third fine particle image in, for example, the internal memory (not illustrated) of the image processor 106 or the memory (not illustrated) of the controller 107.

The image subjected to luminance value adjustment (light-dark processing) is important in recognizing a region where fine particles overlap each other in the logical AND operation on the two images (the second and third fine particle images) in step 203. In a case where fine particles are present with a distribution spreading in the focal direction, even if the fine particles overlap with each other, the decrease amount of the luminance value is small, and the fine particles may not be correctly recognized by merely performing the logical AND operation as in the first embodiment. Therefore, a process of further decreasing the luminance value of the dark region by contrast adjustment (luminance value adjustment 1: step 301) and a process of entirely decreasing the luminance value of the image to darken the image (luminance value adjustment 2: step 302) are performed.

(iii) Step 203

The image processor 106 reads the second fine particle image and the third fine particle image from, for example, the internal memory (not illustrated) of the image processor 106 or the memory (not illustrated) of the controller 107, and performs a logical AND operation on these images. Details of the logical AND operation are as described in the first embodiment.

<Example of Measurement Result>

Figure 8:
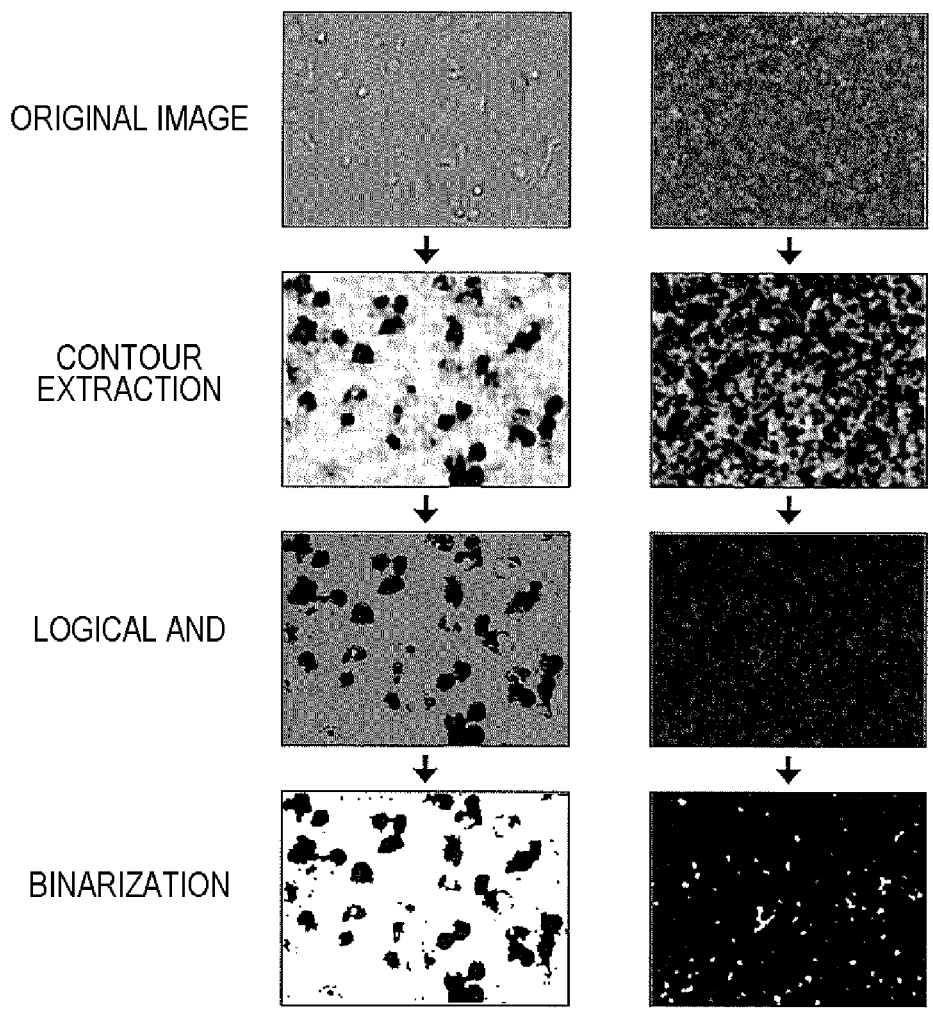
FIGS. 8A to 8B is a diagram illustrating an example of a result (a result obtained by culturing bacteria in a medium containing ampicillin/sulbactam at a concentration of 0.5/0.25 µg/mL or a concentration of 32/16 µg/mL, and plotting the area of bacteria in an image as an example of the feature amount) when image processing (FIG. 7) according to the second embodiment is executed in the fine particle testing apparatus 100.

FIGS. 8A to 8B is a diagram illustrating an example of a result when image processing (FIG. 7) according to the second embodiment is executed in the fine particle testing apparatus 100. From FIG. 8A, it is possible to confirm a state where each fine particle is present in an isolated manner. As compared with the image of fine particles different from those in FIG. 6A, the contours of all the fine particles are not clear, and a state where fine particles having clear contours are present while fine particles having slightly unclear contours and appearing slightly large are present is observed. By using the technique disclosed in the second embodiment, it is possible to prevent erroneous detection of a fine particle region even in such an image. Specifically, by adjusting the luminance value in step 301 and extracting the contour in step 202, fine particles whose contours are unclear can also be extracted as a black region. Then, after the logical AND operation in step 203, a region that has not been recognized as fine particles by contour extraction is recognized as a gray background. Only the region where the fine particles are present can be correctly recognized by the binarization of step 204.

FIG. 8B illustrates images in a case where the number of fine particles increases, and it is possible to confirm a state in which the fine particles appear overlapped with each other. Here, as compared with the image of fine particles different from those in FIG. 6B, the contours of the fine particles cannot be clearly confirmed, but the luminance value of the image is a slightly brighter luminance value. When the contour extraction processing in step 202 is executed, the contour of only the region where the degree of overlapping of the fine particles is locally small and the pixel value is a bright pixel value is recognized, and only a part thereof is extracted as fine particles. This result means that it is not possible, merely by adjusting the contrast, to correctly recognize the region of the fine particles with contour extraction. In the logical operation processing of step 203, a region which satisfies either a dark region having low pixel values in the original image or a dark region having low pixel values after contour extraction is extracted in black. Therefore, it is possible to correctly recognize the region of the fine particles overlapping in the original image.

Effects of Second Embodiment

According to the second embodiment, after contrast adjustment for enhancing a difference in brightness of an image is performed on an image of first fine particles captured by a microscope optical system, an image of second fine particles is calculated by contour extraction. In addition, contrast adjustment is performed on the image of the first fine particles to emphasize a difference in brightness of the image and a third image is calculated. Then, by performing the logical operation on the second and third images, it is possible to correctly recognize the fine particles even in a case where a clear image of fine particles cannot be obtained because the fine particles are present with the distribution spreading in the focal direction of the microscope or in a case where the number of fine particles increases and the entire image is filled with the fine particles.

Note that the luminance value adjustment 2 is not essential. That is, in this case, a logical operation (logical AND operation) is performed between the second fine particle image obtained by extracting the contour after the luminance value adjustment 1 and the first fine particle image. However, as described above, by executing the luminance value adjustment 2 in addition to the luminance value adjustment 1, the process of the luminance value adjustment 1 (contrast adjustment) can be simplified, and the simple process allows the presence of cells (bacteria) having high mobility to be reliably recognized.

(3) Third Embodiment

In a drug sensitivity test for bacteria, it is important to measure properties of bacteria and increase or decrease in the number of bacteria, and in a third embodiment, for example, an example applied to the drug sensitivity test will be described. Also in the third embodiment, the fine particle testing apparatus 100 described in the first embodiment can be used. However, the sample solution 108 contains bacteria, a medium component necessary for growth of the bacteria, and an antimicrobial agent to be tested. The fine particle testing apparatus 100 is temperature-adjusted to a temperature suitable for growth of the bacteria, for example, 37° C. Further, a plate having 96 holes or 384 holes can be used as the testing plate 102.

In a case where the test target is bacteria and the drug sensitivity is tested, it is discriminated at a certain time for each well of the testing plate 102 whether the test results in "proliferation" in which the bacteria proliferate due to ineffectiveness of the antimicrobial agent or "suppression" in which the proliferation of the bacteria is suppressed due to effectiveness of the antimicrobial agent.

<Recognition Result by Image Processing>

Figure 9:
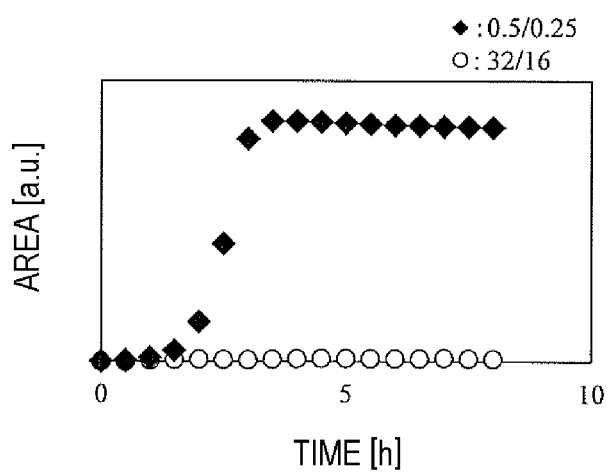
FIG. 9 is a diagram illustrating a relationship (a result obtained by culturing highly motile bacteria in a medium containing gentamicin at a concentration of 0.12 µg/mL or a concentration of 8 µg/mL, and plotting the area of bacteria in an image as an example of the feature amount) of the area of a bacterial region corresponding to the sum of area values of fine particles obtained by executing the processing of steps 200 to 204 (image processing of the first embodiment) on a plurality of time-series images obtained by an imaging part 105 of the fine particle testing apparatus 100.

FIG. 9 is a diagram illustrating a relationship of the area of a bacterial region corresponding to the sum of area values of fine particles obtained by executing the processing of steps 200 to 204 (image processing of the first embodiment) on a plurality of time-series images obtained by the imaging part 105 of the fine particle testing apparatus 100. This measurement result is a result of imaging bacteria cultured for 8 hours in a culture solution containing ampicillin/sulbactam at concentrations of 0.5/0.25 µg/mL and 32/16 µg/mL.

In the case of the concentration of ampicillin/sulbactam of 0.5/0.25 µg/mL, the bacterial area value starts to increase exponentially after 2 hours from the start of culture, and the bacteria fill the entire surface of the imaging range of the microscope in 4 hours to 8 hours. Therefore, the bacterial area value is saturated to a constant value, and a good bacterial growth curve is obtained. In addition, in the case of the concentration of ampicillin/sulbactam of 32/16 µg/mL, the bacterial area value is substantially unchanged from the initial value and becomes constant within 8 hours from the start of culture.

Here, the sensitivity of this bacterium to ampicillin/sulbactam is found to be "proliferation" at a concentration of 0.5/0.25 µg/mL and "suppression" at a concentration of 32/16 µg/mL by turbidity measurement of the well after 18 hours from the start of culture. From FIG. 9, for example, at a lapse of 4 hours, the difference between the bacterial area values at both the concentrations is sufficiently large, and it is possible to discriminate between "proliferation" and "suppression" in a short time. This example has shown that proliferation/suppression is determined at two concentrations of the antimicrobial agent, but actually, the concentration of the drug is more finely changed to determine proliferation/suppression. The minimum antimicrobial agent concentration is referred to as minimum inhibitory concentration (MIC), and the MIC is preferably calculated based on the result of proliferation/suppression. Furthermore, it is determined whether the bacteria of interest are susceptibility (S) or resistance (R) to the antimicrobial agent, or intermediate (I) between the two, in comparison with a so-called breakpoint table.

Figure 10:
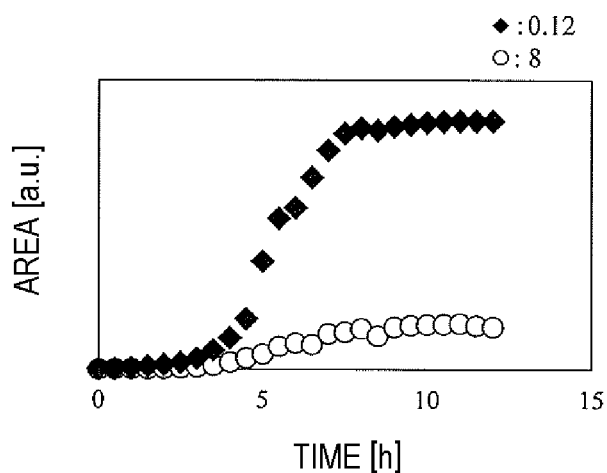
FIG. 10 is a diagram illustrating an example in which the processing of steps 200 to 204 and steps 301 and 302 (image processing of the second embodiment) is executed on a plurality of time-series images obtained by the fine particle testing apparatus 100, and the sum of the area values of the obtained bacterial regions is shown.

In the fine particle testing apparatus 100, an image is acquired by focusing the lens 104 on the vicinity of the well bottom surface of the testing plate 102 for each imaging. However, in a case where the fine particles are bacteria, in particular, highly motile bacteria, even if adjustment is performed for each imaging so as to focus on one well each time, an image with a clear contour may not be acquired, resulting in an image as illustrated in FIGS. 8A to 8B. As an example of such a case, a measurement example using *Pseudomonas aeruginosa* considered to have high motility as a bacterium different from the result of FIG. 9 will be described (see FIG. 10). FIG. 10 is a diagram illustrating an example in which the processing of steps 200 to 204 and steps 301 and 302 (image processing of the second embodiment) is executed on a plurality of time-series images obtained by the fine particle testing apparatus 100, and the sum of the area values of the obtained bacterial regions is shown. This measurement result corresponds to a result of imaging bacteria cultured for 12 hours in a culture solution containing gentamicin at concentrations of 0.12 µg/mL and 8 µg/mL.

Referring to FIG. 10, in the case of the concentration of gentamicin of 0.12 µg/mL, the bacterial area value starts to increase exponentially after 4 hours from the start of culture, and after 8 hours, the bacteria fill the entire surface of the imaging range of the microscope, and therefore, the bacterial area value is saturated to a constant value. In the case of the concentration of gentamicin of 8 µg/mL, a state where the bacterial area value slightly increases is seen after 5 hours from the start of culture, but the difference between the bacterial area values is sufficiently large as compared with the case of 0.12 µg/mL.

Here, the sensitivity of gentamicin to this bacterium is found to be "proliferation" at a concentration of 0.12 µg/mL and "suppression" at a concentration of 8 µg/mL by turbidity measurement after 18 hours from the start of culture, and the difference between the bacterial area values at both the concentrations is sufficiently large, and therefore, it is possible to discriminate between "proliferation" and "suppression" in a short time (the slope of increase in area can be used as an index for determination of increase).

Since the bacterial species used for the drug sensitivity test may be different for each measurement, in the third embodiment, the processing of the first embodiment and the processing of the second embodiment are changed depending on, for example, the bacterial species to be measured. This enables accurate determination.

Figure 11:
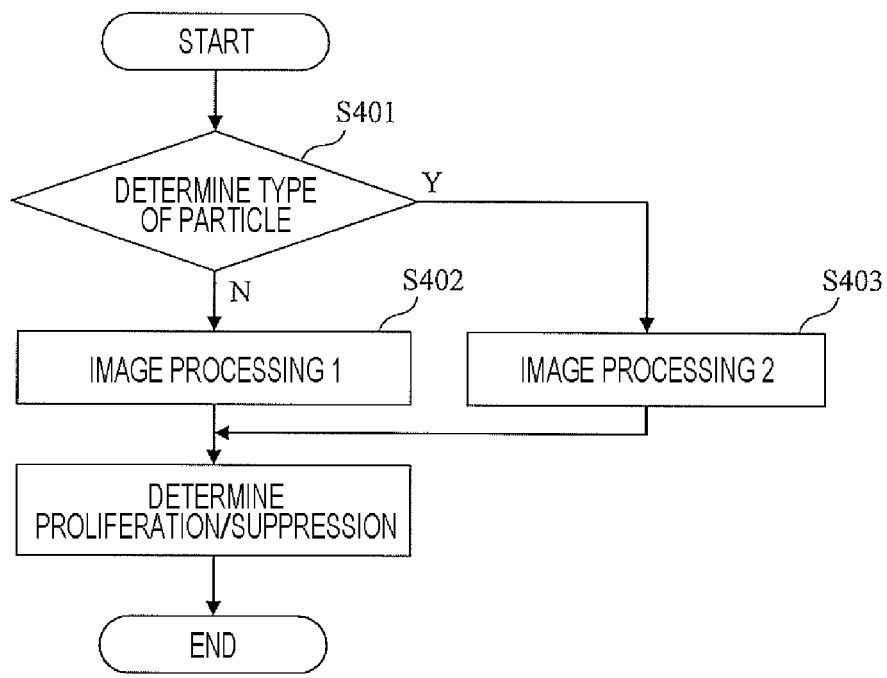
FIG. 11 is a flowchart for explaining a cell proliferation/suppression determination process according to a third embodiment.

FIG. 11 is a flowchart for explaining a cell proliferation/suppression determination process according to the third embodiment.

(i) Step 401

The image processor 106 determines the type of particle, for example, type of bacteria. For example, the determination method is desirably changed in bacteria having low motility and bacteria having high motility, and the motility can be determined by a difference in bacterial species. As an example, the processing of step 401 (particle type determination) may be performed based on the bacterial species information previously input from the user by the controller 107.

In addition, the motility of bacteria and the bacterial species may be determined based on the shape of bacteria in the bacterial image obtained before the image processing is performed, for example, on a moving amount of bacteria between images in a short time frame interval for several seconds.

When the bacteria is determined as a bacterial species having low motility (NO in step 401), the process proceeds to step 402. When the bacteria is determined as a bacterial species having high motility (YES in step 401), the process proceeds to step 403.

(ii) Step 402

The image processor 106 extracts a feature amount by executing the image processing 1 (steps 200 to 205) described in the first embodiment.

(iii) Step 403

The image processor 106 extracts a feature amount by the image processing 2 (steps 200 to 205, step 301, and step 302) described in the second embodiment.

(iv) Step 404

The image processor 106 determines proliferation/suppression by a discriminant formula.

Figure 12:
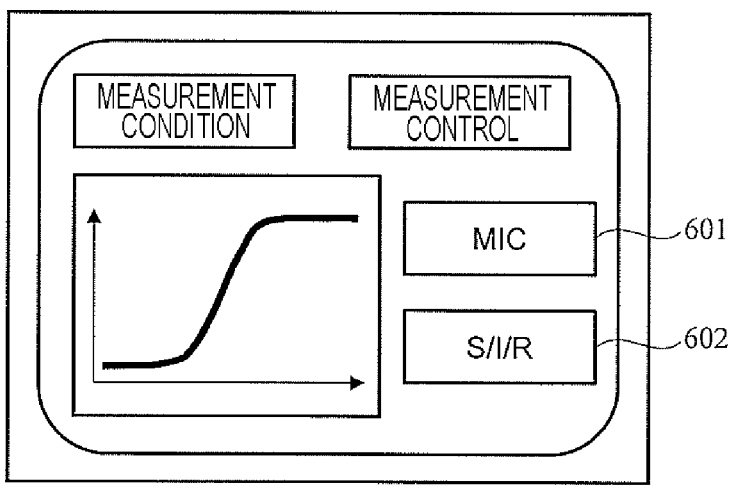
FIG. 12 is a diagram illustrating a configuration example of the graphical user interface (GUI) displayed on the display part 1071 in the third embodiment.

Note that a series of results calculated by the image processor 106 are displayed on the display device of the controller 107 and transmitted to the operator. FIG. 12 is a diagram illustrating a configuration example of the graphical user interface (GUI) displayed on the display part 1071. The GUI displayed on the display part 1071 can be configured to include, for example, the measurement condition input/display area 501, the measurement control state display area 502, the increase curve display area 503, an MIC determination display area 601, and a sensitivity result display area 602 to an antimicrobial agent. Specifically, the GUI can display information on the type of bacteria and the antimicrobial agent as measurement conditions, the determination result of the temporal change of the area of the fine particles obtained in step 205 or the proliferation and suppression of each well, and the result of the MIC or sensitivity (S, I, R) of each antimicrobial agent.

As described above, in a case where the fine particles are bacteria, the shape varies depending on the bacterial species and the environment, and the fine particles present in the image take various forms as the increase in the number of fine particles proceeds by the proliferation.

(4) Summary (i) According to the first embodiment, the imaging part captures a first fine particle image of a well that holds a liquid containing fine particles, and the image processor executes desired image processing on the first fine particle image. For example, the image processor executes a process of generating a second fine particle image by extracting a contour of the first fine particle image, a process of performing a logical operation between the first fine particle image and the second fine particle image, a process of calculating a feature amount of the fine particles based on a result of the logical operation, and a process of determining growth of the fine particles in the well based on the calculated feature amount. Then, the display part (output part) displays (outputs) the result of the growth determination.

(ii) According to the second embodiment, the imaging part captures a first fine particle image of a well that holds a liquid containing fine particles, and the image processor executes desired image processing on the first fine particle image. For example, the image processor executes a process of generating a second fine particle image by performing first luminance value adjustment processing of enhancing a difference in brightness of an image with respect to the first fine particle image to adjust contrast and then extracting a contour of the first fine particle image, a process of performing a logical operation between the first fine particle image and the second fine particle image, a process of calculating a feature amount of the fine particles based on a result of the logical operation, and a process of determining growth of the fine particles in the well based on the calculated feature amount. Then, the display part (output part) displays (outputs) the result of the growth determination. Here, the image processor may generate a third fine particle image by performing second luminance value adjustment processing different from the first luminance value adjustment processing on the first fine particle image, and execute a process of performing a logical operation between the third fine particle image and the second fine particle image instead of the first fine particle image.

(iii) According to the third embodiment, the imaging part captures a first fine particle image of a well that holds a liquid containing fine particles, and the image processor switches between image processing (first image processing) proposed in the first embodiment and image processing (second image processing) proposed in the second embodiment according to the type of fine particles to perform image processing on the first fine particle image, calculates a feature amount of the fine particles, and determines whether the fine particles grow or the growth is suppressed based on the feature amount. Here, the information on the type of fine particles may be input by, for example, an operator (user), or the type of fine particles may be estimated by calculating a moving amount of the fine particles from the first fine particle image, and the estimated type of fine particles may be used as the information on the type of fine particles.

(iv) According to the first to third embodiments, not only in a case where the bacteria exist in an isolated manner, but also in a case where the number of bacteria increases and the entire image is filled with the bacteria or in a case where a clear image of the bacteria cannot be obtained because the bacteria are present with a distribution spreading in the focal direction of the microscope, it is possible to prevent erroneous recognition of the bacterial region and correctly extract the feature amount of the bacteria.

(v) The function of each embodiment can also be realized by a software program code. In this case, a storage medium in which the program code is recorded is provided to a system or a device, and a computer (or a CPU or an MPU) of the system or the device reads the program code stored in the storage medium. In this case, the program code itself read from the storage medium realizes the functions of the above-described embodiments, and the program code itself and the storage medium storing the program code constitute the present disclosure. As a storage medium for supplying such a program code, for example, a flexible disk, a CD-ROM, a DVD-ROM, a hard disk, an optical disk, a magneto-optical disk, a CD-R, a magnetic tape, a nonvolatile memory card, a ROM, or the like is used.

In addition, an operating system (OS) or the like running on a computer may perform a part or all of actual processing based on an instruction of a program code, and the functions of the above-described embodiments may be realized by the processing. Further, after the program code read from the storage medium is written in the memory on the computer, a CPU or the like of the computer may perform a part or all of the actual processing based on an instruction of the program code, and the functions of the above-described embodiments may be realized by the processing.

Furthermore, a program code of software that realizes the functions of the embodiments may be distributed via a network to thereby be stored in a storage means such as a hard disk or a memory of a system or a device or a storage medium such as a CD-RW or a CD-R, and a computer (or a CPU or an MPU) of the system or the device may read and execute the program code stored in the storage means or the storage medium at the time of use.

Finally, it is necessary to understand that the processes and techniques described herein are not inherently related to any particular apparatus and can be implemented by any suitable combination of components. Furthermore, various types of general-purpose devices can be used according to the teaching described here. It may prove advantageous to construct a dedicated apparatus to perform the steps of the method described here. In addition, various inventions can be formed by appropriately combining a plurality of components disclosed in the embodiments. For example, some components may be deleted from all the components shown in the embodiments. Further, the components described in different embodiments may be appropriately combined. Although the present disclosure has been described in connection with specific examples, these are not for limitation but for explanation in all respects. Those skilled in the art will recognize that there are numerous combinations of hardware, software, and firmware suitable for implementing the present disclosure. For example, the described software can be implemented in a program or a script language in a wide range such as assembler, C/C++, perl, Shell, PHP, and Java (registered trademark).

Further, in the above-described embodiments, control lines and information lines considered to be necessary for description are illustrated, and not all the control lines and information lines on a product are necessarily illustrated. All the configurations may be connected to each other.

(vi) The present disclosure is not limited to the above-described embodiments and examples, and includes various modifications. The above-described embodiments have been described in detail in order to describe the technique of the present disclosure in an easy-to-understand manner, and are not necessarily limited to those having all the described configurations. A part of the configuration of one embodiment can be replaced with the configuration of another embodiment, and the configuration of another embodiment can be added to the configuration of one embodiment. In addition, an addition, a deletion, or a replacement of another configuration can be performed with respect to a part of the configuration of each embodiment.

REFERENCE SIGNS LIST 100 fine particle testing apparatus
101 illumination part
102 testing plate
103 stage
104 objective lens
105 imaging part
106 image processor
107 controller
108 sample solution

The invention claimed is:
1. A testing apparatus comprising:
a processor, a memory and a storage;
an imaging device capturing a first fine particle image of a well that holds a liquid containing fine particles, the imaging device in communication with the processor;

an image processor executing a process of generating a second fine particle image by extracting a contour of the first fine particle image, a process of performing a logical operation between the first fine particle image and the second fine particle image, a process of calculating a feature amount of the fine particles based on a result of the logical operation, and a process of determining growth of the fine particles in the well based on the calculated feature amount; and an output device outputting a result of the determination, wherein the imaging device captures, in time series, at least the first fine particle image at a first point of time and the first fine particle image at a second point of time later than the first point of time, and the image processor executes a process of generating, in time series, at least the second fine particle image at the first point of time and the second fine particle image at the second point of time, a process of performing, in time series, at least the logical operation at the first point of time and the logical operation at the second point of time, a process of calculating, in time series, at least the feature amount at the first point of time and the feature amount at the second point of time, and a process of determining growth of the fine particles by comparing the feature amount at the first point of time with the feature amount at the second point of time.

2. The testing apparatus according to claim 1, wherein the image processor calculates an area of a region where the fine particles are present in the first fine particle image as the feature amount of the fine particles.

3. The testing apparatus according to claim 2, wherein the image processor calculates a region where a luminance value locally changes and a region where the luminance value is less than a predetermined value in the first fine particle image, and then calculates an area of a region where the fine particles are present.

4. The testing apparatus according to claim 2, wherein the image processor further calculates, as the feature amount of the fine particles, a shape feature amount including at least one of roundness, a circumferential length, a length of a minor axis or a major axis of the fine particles, and a ratio thereof, and determines an increase in the number of fine particles by combining a plurality of the areas and the shape feature amounts.

5. The testing apparatus according to claim 1, wherein the image processor performs a logical AND operation between the first fine particle image and the second fine particle image.

6. A testing apparatus comprising:

a processor, a memory and a storage;

an imaging device capturing a first fine particle image of a well that holds a liquid containing fine particles, the imaging device in communication with the processor;

an image processor executing a process of generating a second fine particle image by performing first luminance value adjustment processing of enhancing a difference in brightness of an image with respect to the first fine particle image to adjust contrast and then extracting a contour of the first fine particle image, a process of performing a logical operation between the first fine particle image and the second fine particle image, a process of calculating a feature amount of the fine particles based on a result of the logical operation, and a process of determining growth of the fine particles in the well based on the calculated feature amount; and an output device outputting a result of the determination, wherein the imaging device captures, in time series, at least the first fine particle image at a first point of time and the first fine particle image at a second point of time later than the first point of time, and the image processor executes a process of generating, in time series, at least the second fine particle image at the first point of time and the second fine particle image at the second point of time, a process of performing, in time series, at least the logical operation at the first point of time and the logical operation at the second point of time, a process of calculating, in time series, at least the feature amount at the first point of time and the feature amount at the second point of time, and a process of determining growth of the fine particles by comparing the feature amount at the first point of time with the feature amount at the second point of time.

7. The testing apparatus according to claim 6, wherein the image processor execute a process of generating a third fine particle image by performing second luminance value adjustment processing different from the first luminance value adjustment processing on the first fine particle image, and a process of performing a logical operation between the third fine particle image and the second fine particle image instead of the first fine particle image.

8. The testing apparatus according to claim 7, wherein the second luminance value adjustment processing is light-dark adjustment processing of entirely raising or lowering a luminance value of the first fine particle image by a predetermined value.

9. The testing apparatus according to claim 6, wherein the fine particles are bacteria, and the image processor executes a process of determining proliferation and suppression of the bacteria in the well.

10. The testing apparatus according to claim 9, wherein the image processor calculates, as a feature amount of the bacteria, an area of a region where the bacteria are present in the first fine particle image and a shape feature amount including at least one of roundness, a circumferential length, a length of a minor axis or a major axis of the bacteria, and a ratio thereof, and determines proliferation and suppression of the bacteria by combining a plurality of the areas and the shape feature amounts.

11. The testing apparatus according to claim 9, wherein the image processor calculates an area of a region where the bacteria are present in the first fine particle image as the feature amount of the bacteria, and generates a growth curve based on a temporal change in the area of the bacteria, and the output device outputs the growth curve.

12. A testing apparatus comprising:

a processor, a memory and a storage;

an imaging device capturing a first fine particle image of a well that holds a liquid containing fine particles, the imaging device in communication with the processor;

an image processor switching between first image processing and second image processing according to a type of the fine particles to perform image processing on the first fine particle image, calculating a feature amount of the fine particles, and determining whether the fine particles grow or the growth is suppressed based on the feature amount; and an output device outputting a result of the determination, wherein the first image processing includes a process of generating a second fine particle image by extracting a contour of the first fine particle image, a process of performing a logical operation between the first fine particle image and the second fine particle image, and a process of calculating a feature amount of the fine particles based on a result of the logical operation, and the second image processing includes a process of generating a third fine particle image by performing first luminance value adjustment processing of enhancing a difference in brightness of an image with respect to the first fine particle image to adjust contrast and then extracting a contour of the first fine particle image, a process of performing a logical operation between the first fine particle image and the third fine particle image, and a process of calculating a feature amount of the fine particles based on a result of the logical operation.

13. The testing apparatus according to claim 12, wherein the image processor switches between the first image processing and the second image processing based on input information on the type of the fine particles.

14. The testing apparatus according to claim 12, wherein the image processor estimates the type of the fine particles by calculating a moving amount of the fine particles from the first fine particle image captured by the imaging device, and switches between the first image processing and the second image processing based on information on the type of the fine particles.

15. A testing method comprising:

providing a processor, a memory and a storage;

capturing, by an imaging device, a first fine particle image at a first point of time of a well that holds a liquid containing fine particles, the imaging device in communication with the processor;

generating, by an image processor, a second fine particle image at the first point of time by extracting a contour of the first fine particle image at the first point of time;

performing, by the image processor, a logical operation between the first fine particle image at the first point of time and the second fine particle image at the first point of time and generating a first logical operation result;

calculating, by the image processor, a feature amount of the fine particles at the first point of time based on the first logical operation result;

capturing, by the imaging device, the first fine particle image at a second point of time after a lapse of a predetermined time from the first point of time;

generating, by the image processor, a second fine particle image at the second point of time by extracting a contour of the first fine particle image at the second point of time;

performing, by the image processor, a logical operation between the first fine particle image at the second point of time and the second fine particle image at the second point of time and generating a second logical operation result;

calculating, by the image processor, a feature amount of the fine particles at the second point of time based on the second logical operation result;

performing growth determination of the fine particles in the well based on the feature amount of the fine particles at the first point of time and the feature amount of the fine particles at the second point of time; and outputting, by an output device, a result of the growth determination.

* * * * *